US 6,702,778 B2

(12) United States Patent
Hill et al.

(10) Patent No.: US 6,702,778 B2
(45) Date of Patent: Mar. 9, 2004

(54) WET/DRY AUTOMATIC INJECTOR ASSEMBLY

(75) Inventors: Robert Leavitt Hill, Abingdon, MD (US); Maria Cristina D'Erasmo, Colesville, MD (US); John G. Wilmot, Mt. Airy, MD (US); Gerald L. Wannarka, Columbia, MD (US)

(73) Assignee: Meridian Medical Technologies, Inc., Columbia, MD (US)

( * ) Notice: Subject to any disclaimer, the term of this patent is extended or adjusted under 35 U.S.C. 154(b) by 0 days.

(21) Appl. No.: 09/876,255

(22) Filed: Jun. 8, 2001

(65) Prior Publication Data

US 2002/0016563 A1 Feb. 7, 2002

Related U.S. Application Data

(60) Provisional application No. 60/209,974, filed on Jun. 8, 2000.

(51) Int. Cl.[7] .............................................. A61M 37/00
(52) U.S. Cl. .............................. 604/85; 604/82; 604/92
(58) Field of Search .............................. 604/85, 91, 90, 604/92, 84, 191, 236, 82

(56) References Cited

U.S. PATENT DOCUMENTS

| 4,413,991 A | | 11/1983 | Schmitz et al. | |
|---|---|---|---|---|
| 4,529,403 A | | 7/1985 | Kamstra | |
| 4,613,326 A | | 9/1986 | Szwarc | |
| 4,792,329 A | | 12/1988 | Schreuder | |
| 4,822,340 A | * | 4/1989 | Kamstra | 604/90 |
| 4,861,335 A | | 8/1989 | Reynolds | |
| 4,874,381 A | | 10/1989 | Vetter | |
| 4,898,580 A | | 2/1990 | Crowley | |
| 4,983,164 A | * | 1/1991 | Hook et al. | 604/87 |
| 4,994,043 A | | 2/1991 | Ysebaert | |
| 5,041,088 A | | 8/1991 | Ritson et al. | |
| 5,080,649 A | | 1/1992 | Vetter | |
| 5,125,892 A | * | 6/1992 | Drudik | 604/90 |
| 5,281,198 A | | 1/1994 | Haber et al. | |
| 5,290,228 A | * | 3/1994 | Uemura et al. | 604/90 |
| 5,395,323 A | | 3/1995 | Berglund | |
| 5,569,192 A | | 10/1996 | Van der Wal | |
| 5,620,421 A | | 4/1997 | Schmitz | |
| 5,637,087 A | | 6/1997 | O'Neil et al. | |
| 5,725,777 A | | 3/1998 | Taylor | |
| 5,785,683 A | | 7/1998 | Szapiro et al. | |
| 5,876,372 A | * | 3/1999 | Grabenkort et al. | 604/89 |
| 5,971,953 A | | 10/1999 | Bachynsky | |
| 6,319,225 B1 | * | 11/2001 | Sugita et al. | 604/89 |

* cited by examiner

*Primary Examiner*—Brian L. Casler
*Assistant Examiner*—Matthew DeSanto
(74) *Attorney, Agent, or Firm*—Pillsbury Winthrop LLP

(57) ABSTRACT

The present invention is directed to an automatic injection device containing a pre-loaded charge of medicament for automatically self-administering the medicament upon actuation thereof. The automatic injection device includes a dry compartment located within a housing for storing a predetermined dry charge of the medicament therein, a wet compartment within the housing for storing a predetermined amount of liquid injection solution therein, an activation assembly for causing the liquid injection solution in the wet compartment to be transferred to the dry wet compartment, and at least one compression assembly for maintaining the medicament located in the dry compartment under a continuous compressive state as the liquid injection solution passes through the dry compartment.

8 Claims, 2 Drawing Sheets

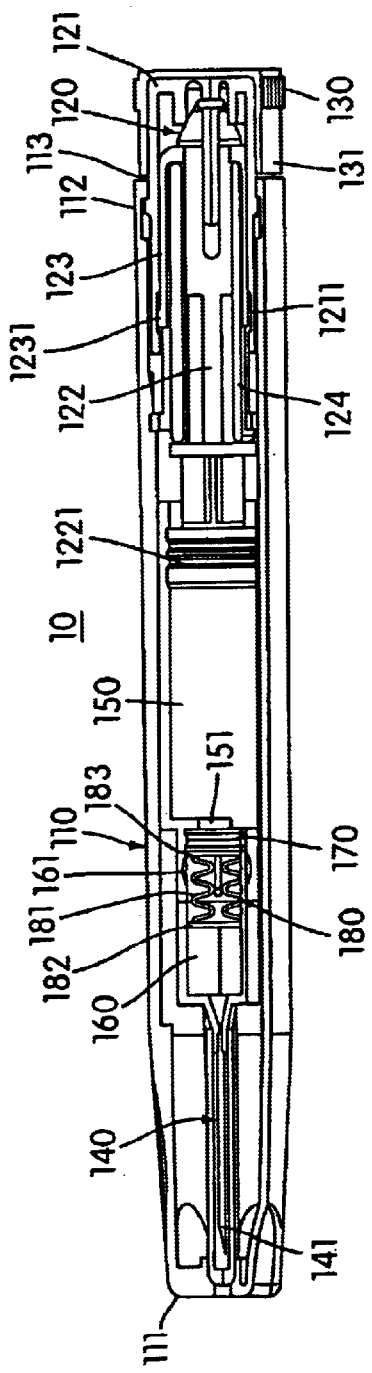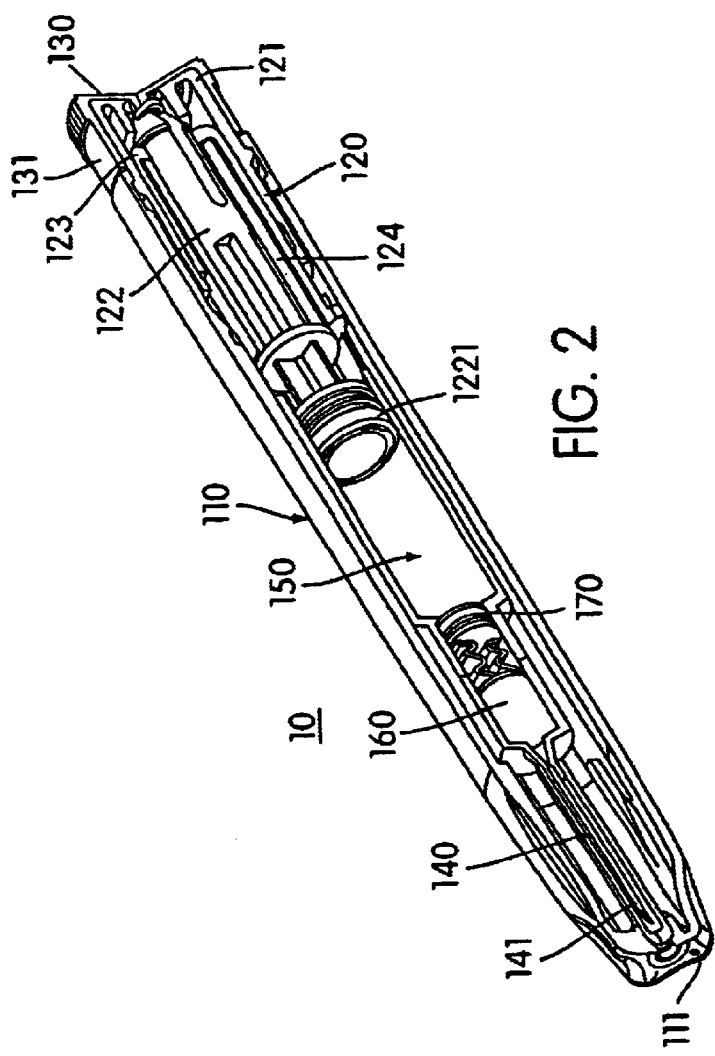

WET/DRY AUTOMATIC INJECTOR ASSEMBLY

CROSS REFERENCE TO RELATED APPLICATION

This application claims priority from U.S. Provisional Serial No. 60/209,974, filed Jun. 8, 2000, and is incorporated herein in its entirety by reference.

FIELD OF THE INVENTION

The present invention relates to automatic injectors for delivering medicament to an injection site. In particular, the present invention is directed to an automatic injector assembly for quickly combining a liquid material with a dry material to form a liquid medicament for delivering the medicament to an injection site.

BACKGROUND OF THE INVENTION

An automatic injector is a device for enabling an individual to self-administer a dosage of medicament into his or her flesh. The medicament is stored in liquid form. The advantage of automatic injectors is that they contain a measured dosage of a liquid medicament in a sealed sterile cartridge and can be utilized for delivering the medicament into the flesh during emergency situations. Another advantage of automatic injectors is that the self-administration of the medicament is accomplished without the user initially seeing the hypodermic needle through which the medicament is delivered and without having the user to manually force the needle into his or her own flesh.

There are drawbacks associated with the storage of medicament in liquid form. Some medicaments are not stable in liquid form. Furthermore, some liquid medicaments typically have a shorter shelf life than their solid counterparts. Others have developed automatic injectors that store the medicament in solid form and a liquid injection solution. These injectors, disclosed for example in U.S. Reissue Pat. No. 35,986, entitled "Multiple Chamber Automatic Injector," (the disclosure of which is incorporated herein specifically by reference), however, require the user of the injector to expedite dissolution of the solid component by manually shaking the liquid component and the solid component immediately prior to injection. This increases the time needed to administer a dose of medicament. Furthermore, the improper mixing of the medicament with the liquid injection solution may release an insufficient dose of medicament. There is a need for an automatic injector that stores medicament in solid form that does not require manual premixing by the user. Furthermore, rapid delivery of the medicament is needed for emergency medical situations (e.g. nerve gas and chemical agent poisoning).

OBJECTS OF THE INVENTION

It is therefore an object of the present invention to provide an automatic injector device that stores medicament in a solid form for increased shelf life.

It is another object of the present invention to provide an automatic injector device that automatically mixes a solid medicament with a liquid injection solution upon activation.

It is another object of the present invention to provide an automatic injector device that stores the solid medicament under pressure to enhance dissolution in the liquid injection solution.

Additional objects and advantages of the invention are set forth, in part, in the description which follows, and, in part, will be apparent to one of ordinary skill in the art from the description and/or practice of the invention.

SUMMARY OF THE INVENTION

In response to the foregoing challenges, applicants have developed an innovative automatic injection device having both wet and dry storage compartments. The present invention is directed to an automatic injection device containing a pre-loaded charge of medicament for automatically self-administering the medicament upon actuation thereof. The automatic injection device may include a housing assembly, a dry compartment located within the housing for storing a predetermined dry charge of the medicament therein, a wet compartment within the housing for storing a predetermined amount of liquid injection solution therein, and an activation assembly for causing the liquid injection solution in the wet compartment to be transferred to the dry compartment. In accordance with the present invention, the medicament located within the dry compartment dissolves in the liquid injection solution as the liquid injection solution passes through the dry compartment to the needle.

The automatic injector in accordance with the present invention further includes at least one compression assembly for maintaining the medicament located in the dry compartment under a continuous compressive state as the liquid injection solution passes through the dry compartment. As such the undissolved medicament is maintained in a compressive state. In accordance with the present invention, the at least one compression assembly is located within the dry compartment. Each compression assembly may include an expandable assembly. The expandable assembly expands as the medicament located within the dry compartment dissolves within the liquid injection solution. The expandable assembly may include a spring assembly and at least one plate to apply pressure on the medicament within the dry compartment. The at least one plate permits the passage of the liquid injection solution therethrough.

The automatic injector in accordance with the present invention further includes a needle assembly for dispensing the liquid injection solution containing the medicament dissolved therein.

The automatic injector in accordance with the present invention may further include a releasable liquid barrier assembly located between the wet compartment and the dry compartment for selectively preventing passage of the liquid injection solution from the wet compartment to the dry compartment at predetermined conditions. It is contemplated that the releasable liquid barrier assembly permits the passage of the liquid injection solution to the dry compartment in response to a predetermined liquid pressure build up within the wet compartment.

In another aspect of the invention, a method for administering an injection of medicament injection solution to a patient using an automatic injection device is provided. Generally, the method comprising locating an injection end of the automatic injection device adjacent a desired injection site on the patient; and activating a drive to advance a collet into a wet compartment of the automatic injection device to pressurize the liquid injection solution in the liquid compartment and to cause an injection needle of the automatic injection device to advance and protrude through the injection end of the automatic injection device. The pressurization of the liquid injection solution causes the liquid injection solution to pass into a dry compartment adjacent the wet compartment where the liquid injection solution mixes with a compressed dry medicament to form a medicament injection solution which is then transmitted through the injection needle to the injection site where it is administered to the patient.

BRIEF DESCRIPTION OF THE DRAWINGS

The invention will be described in conjunction with the following drawings in which like reference numerals designate like elements and wherein:

FIG. 1 is a cross-sectional side view of a wet/dry automatic injector assembly in accordance with the present invention;

FIG. 2 is a partial cross-sectional schematic view of the wet/dry automatic injector assembly of FIG. 1;

DETAILED DESCRIPTION OF THE PREFERRED EMBODIMENTS

Figure 3:
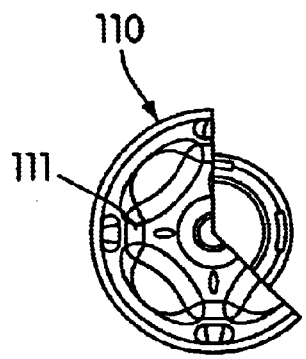
FIG. 3 is a partial cut-away view of the injection end of the wet/dry automatic injector assembly of FIG. 1.

Referring now, more particularly to the figures, there is shown in FIG. 1 an automatic injector assembly 10. The present invention is described in connection with a push button type auto injector, whereby the user removes an end cap assembly and presses a button to trigger the injection process. The present invention, however, is not limited to push button type automatic injectors; rather, it is contemplated that the present invention may be incorporated into a nose activated auto injector, as described for example in U.S. Pat. No. 5,658,259. The disclosures of which are hereby specifically incorporated herein by reference.

The automatic injector assembly 10 includes a generally hollow housing 110. The housing 110 includes an injection insertion end 111 and an activation end 112, as shown in FIG. 1. An actuator assembly 120 extends from an opening 113 in the activation end 112 of the housing 110. The actuator assembly 120 is slidably received within the housing 110. A removable end cap assembly 130 is releasably secured to the actuator assembly 120. When the end cap assembly 130 is secured to the actuator assembly 120, a side portion 131 of the end cap assembly 130 is adapted to abut the housing 110 to prevent movement of the actuator assembly 120 and unintentional injection of the medicament.

The actuator assembly 120 includes a push button actuator assembly 121 having a hollow interior. The end cap assembly 130 engages the push button actuator assembly 121. A collet 122 is located within the hollow interior of the push button actuator assembly 121. An inner tube 123 is also located within the hollow interior of the push button actuator assembly 121. The inner tube 123 is adapted to contact the collet 122, as shown in FIGS. 1 and 2. An opposite end of the inner tube 123 may include an engagement rib 1231 that is adapted to be received within a complementary recess 1211 within the push button actuator assembly 121. A drive assembly 124 is positioned within a space formed between the collet 122 and the inner tube 123.

The drive assembly 124 provides the necessary force when activated to operate the injector to inject the user with a necessary dosage of medicament. It is contemplated that the drive assembly 124 may be a spring assembly, a compressed gas assembly or any other suitable energy storing device. When activated, the drive assembly 124 causes the collet 122 to move such that a needle assembly 140 extends from an opening in the injection end 111 of the housing 110. Movement of the collet 122 also causes mixing of the dry medicament with the liquid injection solution, described in greater detail below.

One end of the collet 122 extends into a wet container 150 located within the housing 110. A sealing assembly 1221 is secured to the end of the collet 122, as shown in FIGS. 1 and 2. The sealing assembly 1221 is adapted to engage the side wall of the wet container 150 to prevent leakage of the contents (e.g. liquid injection solution) of the wet container 150 from the activation end 112 of the housing 110. The sealing assembly 1221 is preferably formed from a material having low frictional properties such that the collet 122 and sealing assembly 1221 may easily slide within the wet container 150 when operated. Alternatively, the sealing assembly 1221 may be lubricated with silicon or other suitable non reactive lubricant. The movement of the collet 122 and the sealing assembly 1221 pressurizes the liquid located within the wet container 150. One end of the wet container 150 opposite the sealing assembly 1221 includes an aperture 151 therein. When pressurized by movement of the collet 122, the liquid exits the wet container 150 through the opening 151 to the dry container 160, which contains the dry medicament in solid form.

A liquid barrier assembly 170 is located adjacent the opening 151 to prevent the inadvertent passage of liquid from the wet container 150 to the dry container 160. As shown, the liquid barrier assembly 170 includes a movable plunger assembly slidably received within the dry container 160. The plunger assembly engages the side wall of the dry container 160 such that liquid does not pass to the dry medicament contained within the dry container 160. As pressure within the wet container 150 increases, the plunger assembly 170 moves away from the opening 151. The dry container 160 includes a recess 161 in a side wall. Liquid may pass from the wet container 150 to the dry container 160 when the plunger assembly 170 is received within the recess 161. The recess 161 allows liquid to flow around the plunger assembly 170 to the dry medicament located within the dry container 160.

The present invention is not limited to the above-described arrangement of the dry container 160 and the wet container 150; rather, other variations are considered to be well within the scope of the present invention. For example, the each of the containers 150 and 160 may the same diameter. Furthermore, a single compartment having a divider assembly may be provided to separate the liquid injector solution from the dry medicament.

The present invention is not limited to the above-described plunger assembly 170; rather, it is contemplated that other liquid barrier assemblies may be employed. The liquid barrier assembly must also prevent vapor transmission between the wet container 150 and the dry container 160. For example, the plunger assembly may be replaced with a barrier layer. The barrier layer would distort and subsequently rupture upon a sufficient build up of pressure within the wet container 150. The barrier layer may be formed from any suitable non reactive impermeable material that could rupture at a predetermined pressure.

Figure 4:
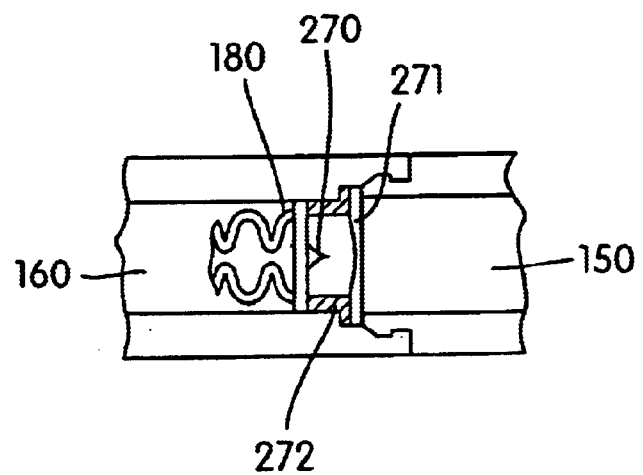
FIG. 4 is a partial schematic view of a barrier layer assembly of the wet/dry automatic injector assembly according to another embodiment of the present invention.

It is also contemplated that the barrier layer may be pierced by a piercing element located within the housing 110. For example, a piercing element may extend from the sealing assembly 1221 such that upon a predetermined movement of the collet 122, the piercing element pierces the barrier layer to permit the liquid to flow from the wet container 150 to the dry container 160. Alternatively, the liquid barrier assembly may include a piercing element 270 extending from a compression element 180, as shown in FIG. 4. As pressure within the wet container 150 increases the barrier layer 271 distorts. A puncture within the barrier layer 271 is created when the layer 271 contacts the piercing element 270. A retainer assembly 272 may be located between the barrier layer 271 and the compression element 180 such that a sufficient distance exists between the barrier layer 271 and the piercing element 270 to allow for a sufficient build up in pressure.

The dry container 160 will now be described in greater detail. A suitable medicament is located within the dry container 160. It is contemplated that the dry medicament may be in either powder or freeze-dried form. To aid in the mixture of the dry medicament with the liquid injection solution contained in the wet container 150, it is desirable that the medicament be maintained in a compressed state while in the dry container 160. Maintaining the dry medicament under compression during to injection, accelerates the dissolution of the solid medicament into the liquid injection solution. Furthermore, this prevents the liquid injection solution entering the dry container 160 from forming channels within the dry medicament, which would impede dissolution of the medicament within the solution. As such, liquid injection solution containing less than the necessary dosage of medicament may be injected into the user. The compression element 180 prevents this phenomenon.

The compression element 180, illustrated in FIG. 1, includes at least one assembly having the ability to expand to compensate for the dissolution of the medicament within dry compartment 160. The compression element 180 may include a spring assembly 181 sandwiched between a pair of liquid permeable plates 182 and 183. It is contemplated that any suitable spring assembly may be employed provided that the expansion of the spring assembly is capable of compensating for the dissolution of the medicament within the dry compartment 160 such that undissolved dry medicament is maintained in a compressed state. The spring assembly may be formed from a non-reactive stainless steel material. Other materials having similar non-reactive properties are considered to be well within the scope of the present invention. Furthermore, it is contemplated that the spring assembly may be coated with a suitable non-reactive material including, but not limited to Teflon®.

The embodiment of the present invention illustrated in FIGS. 1 and 2 illustrates a single compression element 180 located within the dry compartment 160. It, however, is contemplated that additional compression elements may be employed. For example, the medicament located within the dry compartment 160 may be sandwiched between a pair of compression elements. Each compression element may include the above described spring assembly and liquid permeable plates. An example of this arrangement is illustrated in FIGS. 14 and 15 of U.S. Pat. No. 5,725,777 to Taylor, entitled "Reagent/Drug Cartridge," the disclosure of which is incorporated herein specifically by reference.

The liquid injection solution mixed with the medicament may then exit the dry compartment 160 through the needle assembly 140 opposite the wet compartment 150. In the event that two compression elements are utilized, the liquid injection solution mixed with the medicament will pass through one of the compression elements to the needle assembly 140 prior to exiting through the opening. A filter assembly, not shown, may be located adjacent the needle assembly 140 to prevent any undissolved medicament from entering the needle assembly 140. Additionally, a liquid impermeable membrane, not shown, may be provided to prevent the undesired passage of liquid in the event the liquid inadvertently enters the dry compartment 160. The membrane may be either be punctured by the injection assembly 140 or rupture upon the build up of a sufficient amount of pressure.

As discussed above, the movement of the collet 122 and drive assembly 124 causes the injection needle 141 of the injection assembly 140 to advance and protrude through the housing 110. The injection of the medicament can be performed with a simple operation. The user simply removes the end cap assembly 130, locates the injection end of the housing 110 adjacent the injection site and presses the push button actuator assembly 121. This operation automatically triggers the operation of the drive assembly 124 to advance the collet 122 causing the liquid injection solution located within the wet compartment 150 to enter the dry compartment 160. The dissolved medicament is then transmitted through the injection needle 141 to provide the user with the necessary dose of medicament. The automatic injector in accordance with the present invention reduces the amount of time required to administer medicament compared to other wet/dry injectors. The present invention eliminates the need for mixing by the user.

It will be apparent to those skilled in the art that various modifications and variations may be made without departing from the scope of the present invention. For example, it is contemplated that a cover assembly, described for example in U.S. Pat. No. 5,295,965 (the disclosure of which is specifically incorporated herein by reference) may be secured to the injection end of the housing 110 after deployment of the medicament. Furthermore, the automatic injector may further include a nipple plunger assembly, as described for example in U.S. Pat. No. 5,295,965 (the disclosure of which is specifically incorporated herein by reference). Thus, it is intended that the present invention covers the modifications and variations of the invention, provided they come within the scope of the appended claims and their equivalents.

What is claimed is:

1. An automatic injection device containing a pre-loaded charge of medicament for automatically self-administering the medicament upon actuation thereof, said automatic injection device comprising:

a housing assembly;

a dry compartment for storing a predetermined dry charge of dry medicament therein;

a wet compartment for storing a predetermined amount of liquid injection solution therein;

a pre-loaded activation assembly for causing the liquid injection solution in said wet compartment to be transferred to said dry compartment, wherein the pre-loaded activation assembly automatically supplies a driving force upon activation to transfer the liquid injection solution in the wet compartment to the dry compartment, wherein the dry medicament dissolves in the liquid injection solution as the liquid injection solution passes through said dry compartment;

at least one dynamic spring compression assembly for maintaining the dry medicament located in said dry compartment under a continuous compressive state as the liquid injection solution passes through said dry compartment, wherein at least a portion of a compressive force acting on the dry medicament located in said dry compartment is provided by said at least one dynamic spring compression assembly; and a needle assembly for dispensing the liquid injection solution containing the medicament dissolved therein.

2. The automatic injection device according to claim 1, wherein said at least one spring compression assembly is located within said dry compartment.

3. The automatic injection device according to claim 1, wherein said at least one spring compression assembly includes an expandable assembly, wherein said expandable assembly expands within the dry compartment as the medicament located within said dry compartment dissolves within the liquid injection solution.

4. The automatic injection device according to claim 3, wherein the expandable assembly includes a spring assembly and at least one plate to apply pressure on the medicament within said dry compartment.

5. The automatic injection device according to claim 4, wherein said at least one plate permits the passage of the liquid injection solution therethrough.

6. The automatic injection device according to claim 1, further comprising a releasable liquid barrier assembly for selectively preventing passage of the liquid injection solution from said wet compartment to said dry compartment at predetermined conditions.

7. The automatic injection device according to claim 6, wherein said releasable liquid barrier assembly permits the passage of the liquid injection solution to the dry compartment in response to a predetermined liquid pressure build up within said wet compartment.

8. A method for administering an injection of medicament injection solution to a patient using an automatic injection device, said method comprising:

locating an injection end of the automatic injection device adjacent a desired injection site on the patient;

activating a pre-loaded drive to automatically advance a collet into a wet compartment of the automatic injection device to pressurize the liquid injection solution in the liquid compartment and to cause an injection needle of the automatic injection device to advance and protrude through the injection end of the automatic injection device;

wherein the pressurization of the liquid injection solution causes the liquid injection solution to pass into a dry compartment adjacent the wet compartment where the liquid injection solution mixes with a compressed dry medicament to form a medicament injection solution which is then transmitted through the injection needle to the injection site where it is administered to the patient; and maintaining the compressed dry medicament under a continuous compressive state using at least one dynamic spring compression assembly located within the automatic injection device.

* * * * *

UNITED STATES PATENT AND TRADEMARK OFFICE
CERTIFICATE OF CORRECTION

PATENT NO. : 6,702,778 B2 Page 1 of 1
DATED : March 9, 2004
INVENTOR(S) : Robert Leavitt Hill et al.

It is certified that error appears in the above-identified patent and that said Letters Patent is hereby corrected as shown below:

<u>Title page,</u>
Item [75], Inventors, replace "John G. Wilmot, Mt. Airy, MD (US)" with -- John G. Wilmot, Mt. Airy, MD (UK) --.

Signed and Sealed this

Nineteenth Day of October, 2004

JON W. DUDAS
*Director of the United States Patent and Trademark Office*